United States Patent
Gibson et al.

(10) Patent No.: US 10,303,248 B2
(45) Date of Patent: May 28, 2019

(54) EYE TRACKING USING SCANNED BEAM AND MULTIPLE DETECTORS

(71) Applicant: Microsoft Technology Licensing, LLC, Redmond, WA (US)

(72) Inventors: Gregory Theodore Gibson, Seattle, WA (US); Joshua Owen Miller, Woodinville, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 57 days.

(21) Appl. No.: 15/582,353

(22) Filed: Apr. 28, 2017

(65) Prior Publication Data

US 2018/0314325 A1 Nov. 1, 2018

(51) Int. Cl.
| | |
|---|---|
| G02B 27/01 | (2006.01) |
| G06F 3/01 | (2006.01) |
| A61B 3/113 | (2006.01) |
| G02B 26/10 | (2006.01) |
| G06F 3/03 | (2006.01) |
| G06K 9/00 | (2006.01) |
| G02B 27/00 | (2006.01) |

(52) U.S. Cl.
CPC .............. *G06F 3/013* (2013.01); *A61B 3/113* (2013.01); *G02B 26/105* (2013.01); *G02B 27/0093* (2013.01); *G02B 27/017* (2013.01); *G06F 3/0304* (2013.01); *G06K 9/00604* (2013.01); *G02B 2027/014* (2013.01); *G02B 2027/0138* (2013.01)

(58) Field of Classification Search
CPC ..... G06F 3/013; G06F 3/0304; G02B 26/105; G02B 27/017; G02B 2027/014; G02B 2027/0138; A61B 3/113
See application file for complete search history.

(56) References Cited

U.S. PATENT DOCUMENTS

| | | | |
|---|---|---|---|
| 4,836,670 A | 6/1989 | Hutchinson | |
| 7,522,344 B1 | 4/2009 | Curatu et al. | |
| 8,824,779 B1 | 9/2014 | Smyth | |
| 2004/0080467 A1 | 4/2004 | Chinthammit et al. | |
| 2004/0174496 A1* | 9/2004 | Ji | G06F 3/013 351/209 |
| 2004/0227699 A1 | 11/2004 | Mitchell | |
| 2005/0189503 A1 | 9/2005 | Jamieson et al. | |

(Continued)

OTHER PUBLICATIONS

Curatu, et al., "Dual Purpose Lens for an Eye-Tracked Projection Head-Mounted Display", In Proceedings of International Society for Optics and Photonics, Jan. 14, 2007, 7 pages.

(Continued)

*Primary Examiner* — Ibrahim A Khan
(74) *Attorney, Agent, or Firm* — Alleman Hall Creasman & Tuttle LLP

(57) ABSTRACT

Examples are disclosed herein that are related to eye tracking using scanned beam imaging and multiple photodetectors. One example provides an eye tracking system, comprising an infrared light source, scanning optics configured to scan light from the infrared light source across a region comprising a user's cornea, and a plurality of photodetectors, each photodetector being configured to detect infrared light reflected from the user's cornea at a corresponding angle.

19 Claims, 6 Drawing Sheets

(56) References Cited

U.S. PATENT DOCUMENTS

| | | | |
|---|---|---|---|
| 2008/0151185 A1* | 6/2008 | Saito | A61B 3/12 |
| | | | 351/206 |
| 2011/0043644 A1 | 2/2011 | Munger et al. | |
| 2012/0139817 A1 | 6/2012 | Freeman | |
| 2013/0021373 A1* | 1/2013 | Vaught | G02B 27/017 |
| | | | 345/633 |
| 2013/0077049 A1* | 3/2013 | Bohn | G02B 5/20 |
| | | | 351/210 |
| 2013/0114850 A1* | 5/2013 | Publicover | G06K 9/00604 |
| | | | 382/103 |
| 2013/0208362 A1 | 8/2013 | Bohn et al. | |
| 2014/0138544 A1 | 5/2014 | Sprague et al. | |
| 2014/0354514 A1* | 12/2014 | Aronsson | G06F 3/013 |
| | | | 345/7 |
| 2015/0098620 A1 | 4/2015 | Wu et al. | |
| 2015/0131051 A1 | 5/2015 | Huang | |
| 2015/0199006 A1 | 7/2015 | He et al. | |
| 2015/0278576 A1* | 10/2015 | Horesh | G06K 9/0061 |
| | | | 382/103 |
| 2016/0081547 A1 | 3/2016 | Gramatikov et al. | |
| 2016/0270656 A1* | 9/2016 | Samec | A61B 3/085 |
| 2017/0000341 A1 | 1/2017 | Samec et al. | |
| 2017/0115483 A1* | 4/2017 | Aleem | G02B 27/0093 |
| 2018/0120559 A1* | 5/2018 | Yeoh | G02B 26/123 |

OTHER PUBLICATIONS

"International Search Report & Written Opinion Issued in PCT Application No. PCT/US2018/026641", dated Jun. 25, 2018, 15 Pages.

\* cited by examiner

EYE TRACKING USING SCANNED BEAM AND MULTIPLE DETECTORS

BACKGROUND

Eye tracking may be used in computing systems for various applications, such as an input mechanism for a near-eye display system.

SUMMARY

Examples are disclosed herein that are related to eye tracking using scanned beam imaging and multiple detectors. One example provides an eye tracking system, comprising an infrared light source, scanning optics configured to scan light from the infrared light source across a region comprising a user's cornea, and a plurality of photodetectors, each photodetector being configured to detect infrared light reflected from the user's cornea at a corresponding angle.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Figure 1:
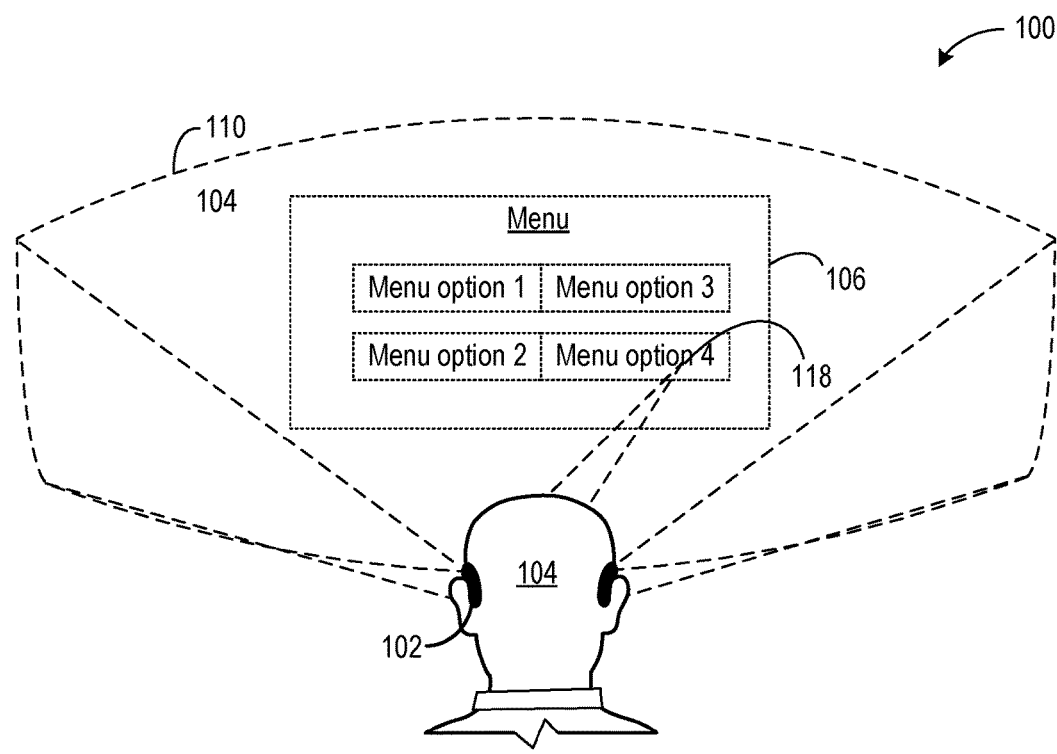
FIG. 1 shows an example use scenario for eye tracking on a near-eye display device.

Eye tracking for computing devices may be implemented in various manners. As one example, an eye tracking system may utilize a plurality of light sources, and an image sensor to capture images of the pupil and of reflections (glints) of the light sources from the cornea. However, such image sensors may be relatively expensive, and may pose problems in some types of display systems, such as augmented reality display systems in which virtual imagery is mixed with a view of a real-world environment. For example, a direct view camera for eye tracking may be positioned in a field of view of a user, and thus impede mixed-reality display within that portion of the field of view. An off-axis camera also may be impractical, as the larger the field of view for the display, the farther the camera would need to be off-axis in order not to occlude the field-of-view. Such an off-axis configuration may pose challenges for image processing.

Accordingly, examples are disclosed herein that relate to eye tracking systems that utilize scanned beam imaging and a plurality of photodetectors. The scanned beam imaging utilizes an infrared light source and scanning optics, such as one or more scanning mirrors, configured to scan light from the infrared light source across a region of a user's eye. Each photodetector is positioned to detect infrared light reflected from the user's cornea at a corresponding angle. As described in detail below, this configuration allows the acquisition of pupil images from light that is diffusely scattered by a user's eye at each angular position (pixel) of the scanning mirror system, and also the determination of specific "glint" locations at which light from the light source is specularly reflected from the user's cornea into each photodetector. The use of multiple photodetectors in combination with a scanned light source may be less costly than the use of an image sensor, while also allowing the detection of glint locations.

The disclosed examples further may utilize separately controllable pipelines for determining pupil locations and glint locations. A pupil location processing pipeline may be configured to produce a signal derived from the outputs of the multiple photodetectors that is representative of an intensity of light scattered from the user's eye. This signal may be input into a frame buffer as a function of the mirror system scanning angle to produce a greyscale image of the user's eye that captures the pupil. Likewise, the glint location processing system may be configured to determine the locations of glints from the cornea of an eye based upon sensing specular reflections at each photodetector. The greyscale image and the glint locations then may be input into an eye tracking algorithm to determine eye gaze direction.

In some examples, the pupil location processing system may operate at a lower frame rate in some circumstances compared to the glint location processing system (or be temporarily disabled) when the output from the glint location processing system indicates that eye rotational movement is less than a threshold magnitude. The pupil location processing system may then switch on and/or operate at a higher frame rate upon detecting that rotational movement of the eye has exceeded the threshold magnitude. This may help to reduce overall power consumption by the system compared to operating both pipelines at a same frame rate at all times, yet rapidly provide updated pupil image data as needed.

Further, in some examples, the glint location processing system may have a different gain than that of the pupil location processing system. As glints may have much higher amplitudes (e.g. one hundred times higher) than diffusely scattered light, the dual path configuration may reduce the dynamic range required in any one path.

FIG. 1 shows an example scenario 100 for use of eye tracking on a near-eye display device 102 worn by a user 104. The near-eye display device 102 may be implemented as an augmented reality display device that utilizes a see-through display to superimpose virtual imagery over a real-world background being viewed, or may capture video of the real-world background and composite the video with virtual imagery for display. In other examples, the near-eye display device 102 may be implemented as a virtual reality display device that displays fully virtual imagery. As shown, a user's gaze direction 102 as determined from eye tracking may be used to detect a user input in a virtual menu 106 being displayed by the near-eye display device 102 to appear at a distance in front of the user 104. Eye tracking may also be used for other human-computer interactions, such as visual attention analysis, and foveated display.

The near-eye display device 102 may utilize a laser light source, one or more microelectromechanical systems (MEMS) mirrors, and potentially other optics (e.g. a waveguide) to produce and deliver an image to a user's eye. In such an example, the eye tracking system may leverage such existing display system components, which may help to reduce a number of components used in manufacturing device 102. For example, by adding an appropriately configured infrared laser for eye illumination, an existing MEMS mirror system used for scanning image production also may be used to scan the light from the eye tracking illumination source across the user's eye. Photodetectors such as photodiodes may be provided at suitable locations to capture specular reflections from the user's cornea for glint tracking, and to capture diffusely scattered light for greyscale imaging. Leveraging existing image display system components for eye tracking may allow the eye tracking illumination source to be presented to the eye on a same or similar axis as that of the display imagery without impeding a view of a real world background, and thus may be suitable for use in augmented reality display systems.

The scanning system may take any suitable form. For example, the scanning system may comprise two mirrors in which one harmonically oscillates to rapidly scan light in a first direction and the other scans more slowly in an orthogonal second direction. In other examples a single scanning mirror may be used, or any other suitable scanning optics. In some examples, the light may be delivered from the scanning system to the user's eye by a waveguide, as mentioned above. In other examples, another component, such as a see-through mirror positioned in front of the eye, may be used to direct light to the eye. In either instance, light may be directed to the eye without having to place a scanning system directly in front of the eye. The system may be configured to overscan the corneal region of the eye to accommodate for varying interpupillary distances, eyeball rotations, and eye reliefs across users.

Figure 2:
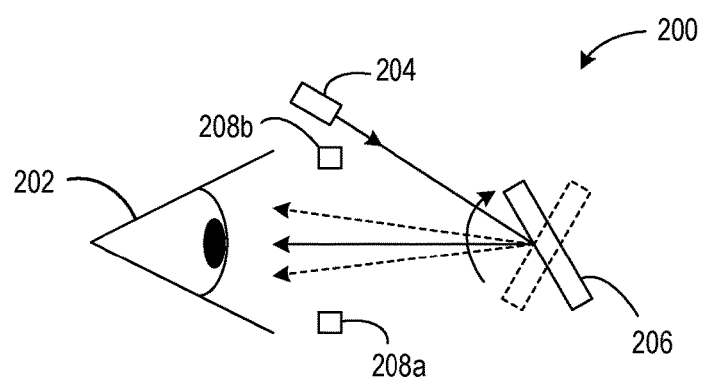
FIG. 2 is a schematic diagram showing an example eye tracking system.

FIG. 2 schematically shows an example eye tracking system 200 that may be incorporated into a near-eye display system, such as the system of FIG. 1, for tracking a user's eye 202. The eye tracking system 200 includes an infrared light source 204, which may take the form of a laser, a light-emitting diode, or other suitable emitter. Light emitted by the infrared light source 204 is received at a scanning MEMS mirror system 206 that scans the light across a region of the eye 202. The scanning mirror system 206 may include a single mirror that scans in two dimensions, or may include separate mirrors that each scan in one direction orthogonal to the direction of the other mirror. As the light is scanned across the eye 202, the light reflects from the eye 202 in directions based upon the angle at which the light is incident on the surface of the eye 202. Reflected light is detected via a plurality of photodetectors 208. In the depicted example, two photodetectors are shown respectively at 208a and 208b, though it will be understood that any suitable number of photodetectors may be used. In some examples, the number of photodetectors present may depend on the eye tracking algorithm utilized by the computing system. Further, in some examples, rather than separately located photodiodes, the photodetectors may take the form of a linear array, or any other suitable form.

As the infrared light scans across the eye, each photodetector receives light that is scattered by the cornea. Each photodetector also receives, at specific scanning system angles, specularly reflected light based upon the location of the photodetector and the rotational position of the eye. Lower-intensity scattered light is used to form a greyscale image of the scanned region of the eye 202 in a pupil location processing system, and higher-intensity specular reflections are utilized to determine glint locations. For pupil location processing, the signals from the plurality of photodetectors may be sampled and computationally combined (e.g. summed) at each angular position of the scanning mirror system 206 to form a bitmap image for use in identifying a location of a pupil. Summing the signals from multiple photodetectors may provide a higher signal-to-noise ratio than using a single sensor for detecting scattered light. Specular reflections may be processed by recording a time stamp and an angular position at which the higher intensity of the specular reflection is received at that photodetector, and changes in the relative locations of the glints may be used to provide information regarding eye rotation. As mentioned above, eye rotation information from glint tracking may be used to control a frame rate of a pupil location processing system in some examples.

Figure 3:
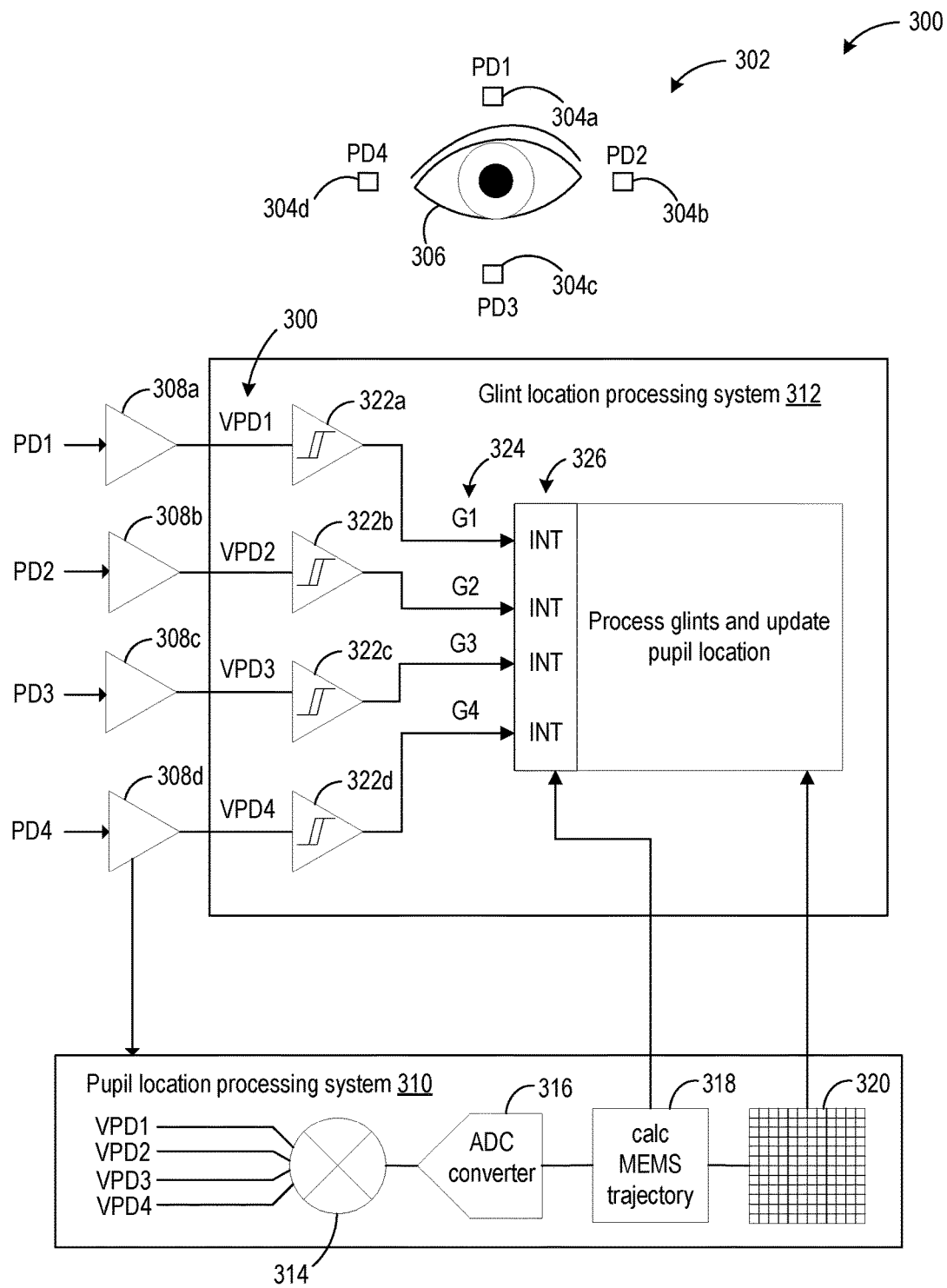
FIG. 3 shows a schematic representation of example processing pipelines in an eye tracking system.

FIG. 3 shows a schematic representation of an example eye tracking process pipeline 300. The example process described herein is in regard to one sample period, and in the context of an eye tracking system 302 having four photodetectors 304. Each photodetector 304 is configured to detect a light reflected by the eye 306 from a scanned beam, such as a laser light source and scanning mirror system. The scanned light may be delivered to the eye 306 via any suitable optics, such as via a waveguide. Each photodetector 304 outputs a signal, represented by PD1, PD2, PD3, and PD4, that is fed into a corresponding current to voltage converter, such as a transimpedance amplifier (TIA), respectively shown at 308a-d. The current to voltage converters 308 output voltages VPD1, VPD2, VPD3, and VPD4 respectively for each photodetector. From here, the process splits into two processing pipelines: a pupil location processing system 310 and a glint location processing system 312.

Referring first to the pupil location processing system 310, the voltage signals are input to a summing junction 314 that sums the voltages, which increases the signal amplitude as well as reduces noise proportionally to the square root of the sum. Next, an analog to digital converter 316 converts the voltage sum signal, still analog, to a digital signal representing the intensity values for reflected light detected for the sample period. A MEMS trajectory calculator 318 receives synchronized signals from the MEMS scanning mirror, which are signals that indicate a current scan x-position and y-position of the scanning mirror during the sample period. The calculator 318 calculates the current scan angle based on the synchronized signals. Based on the scan angle, the summed digital signal output by the analog to digital converter 316 is stored into a corresponding pixel in a frame buffer 320 for that particular angle. Thus, as the mirror rotates and light is scanned across the eye 306, a determined digital sum is stored in the appropriate pixel for each different scan angle, eventually resulting in a full frame buffer with each pixel storing a detected intensity signal, forming a greyscale image. The formed greyscale image may then be analyzed to determine a location of a pupil in the image. In this example, as four photodetectors are used, the greyscale image would have four bright spots in the image, corresponding to where glints are located.

More accurate locations of the glints may be determined by the glint location processing system 312. The voltage signals from the photodetectors 304 and current to voltage converters 308 are also input to comparators 322a-d. Each comparator 322 is configured to compare the received voltage with a reference voltage, and output a digital state 324 based on the comparison, represented by G1, G2, G3 and G4. For example, each digital state 324 may take the form an output bit, such that when the received voltage signal exceeds a reference voltage, the output bit flips. The reference voltage at each comparator may be set, for example, to half the total glint amplitude, or to any other suitable value. Next, each of the output digital states G1-4 is received at an interrupt 326. When a digital signal changes state, the corresponding interrupt 326 may be triggered to store a current time value, e.g. a clock state of an operating clock. The output results in a generated list of glint events with time, each glint having a corresponding time value. A similar MEMS trajectory calculator as described above may be utilized by the glint location processing system 312 to associate each time value with a current MEMS scan angle. The location of a glint may then be calculated using the known mirror scan angle at the time that glint hit a corresponding photodetector. Thus, glint locations may be determined using comparator outputs, without performing image analysis. This may allow glint tracking to be performed in a power-efficient manner. As mentioned above, the glint locations and the determined pupil location from the greyscale image may be provided to an eye tracking algorithm to determine an eye gaze direction.

Pupil location processing may consume more power than glint location processing at a same frame rate. As such, the pupil location processing system 310 may be configured to be inactive or operate at a lower frame rate until a threshold magnitude of eye rotation is detected via the glint location processing system 312 system. The eye tracking algorithm may use a most recent pupil image stored in the frame buffer for gaze determination until eye rotation of sufficient magnitude is determined from the glint location processing system 312 occurs to trigger operation of (or a higher frame rate of operation for) the pupil location processing system 312. This may help to conserve system power.

Figure 4:
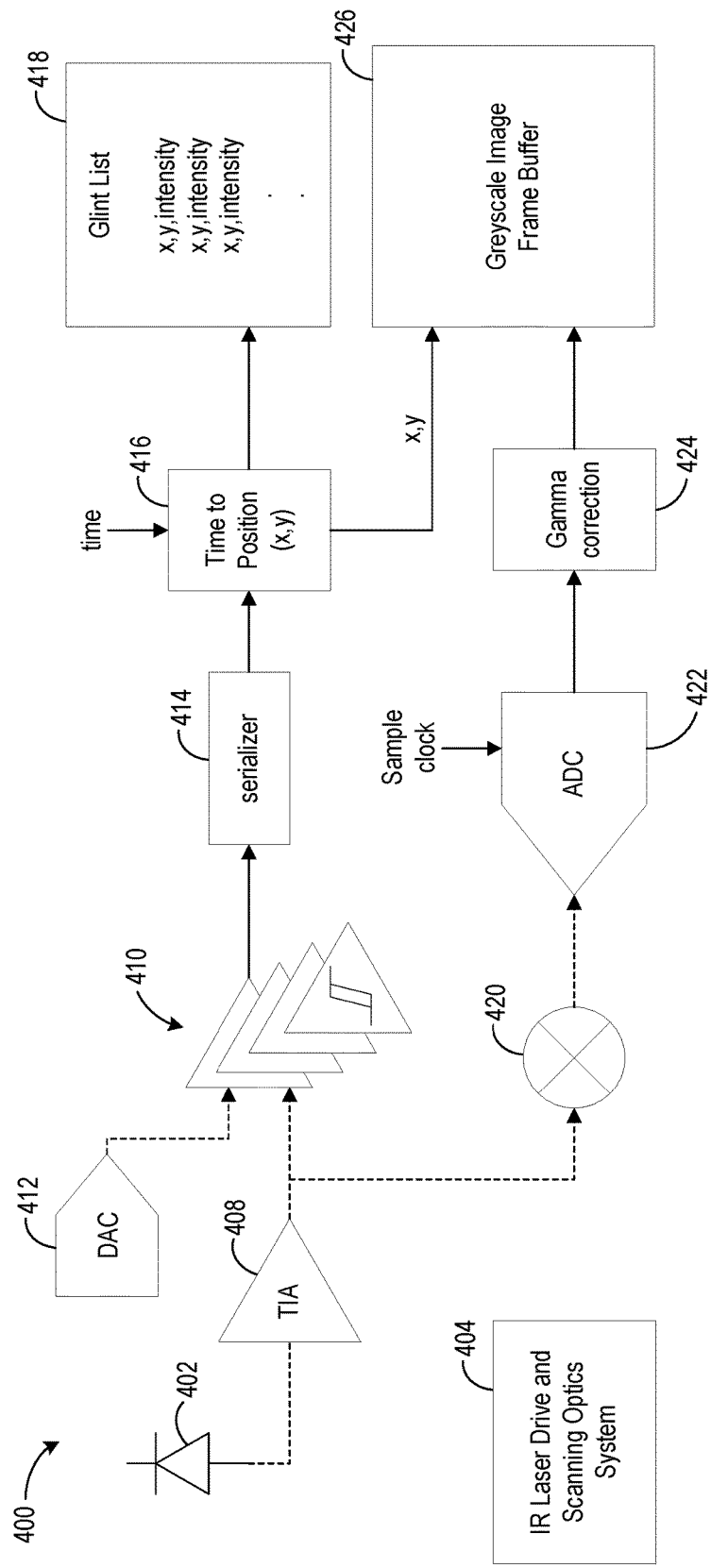
FIG. 4 shows a schematic representation of example processing pipelines in another eye tracking system.

FIG. 4 shows another example eye tracking process pipeline 400. The example pipeline 400 is described and illustrated in the context of one photodetector 402, but it will be understood that the system and processes described may apply to each of a plurality of photodetectors in a system. The photodetector 402 detects light as reflected by an eye illuminated by an infrared laser source controlled by an infrared laser drive and scanning mirror system (not shown). The signal output by the photodetector 402 is received at a current to voltage converter (e.g. TIA) 408, which outputs a voltage signal. Process 400 is similar to process 300 except that the voltage signal resulting from each photodetector is split into four paths for provision to four comparators 410. Each comparator 410 compares the received voltage to a different programmable reference voltage, as received from a digital to analog converter 412, and outputs a digital state accordingly. For example, instead of a 1-bit analog to digital converter, each comparator may utilize a 2- or 3-bit analog to digital converter that allows for more precise amplitude information. Comparing the voltage signal for each photodetector to four different reference voltages may result in a more accurate determination of the amplitude profile of a glint, and thus can be used to accept or reject certain glints based on the voltage amplitudes and/or profiles. For example, the process may help to distinguish a specular reflection from a cornea from a specular reflection from an eyeglass or contact lens, such as by ignoring signals that match an expected voltage amplitude from eyeglasses and/or contact lenses, e.g. as determined during calibration. The use of a plurality of comparators also allows for the creation of a heat map of an amplitude profile for each glint.

Next, a serializer 414 takes the parallel signals (four for each photodetector) and serializes the signals, feeding the signals from each comparator in serial to the next stage. In other examples, the signals may be communicated partially or fully in parallel. Corresponding interrupts, as described above with regard to FIG. 3, may trigger the capture of time values associated with each glint signal, and the acquisition (e.g. from a MEMS trajectory calculator) synchronized signals from the MEMS scanning mirror indicating a current scan x-position and y-position of the scanning mirror, as shown at 416. A glint list 418 is then formed with each glint having a corresponding intensity (amplitude) and x and y position of the scanning mirror. Based on the mirror position, the system determines the angle of reflection, and also determine the glint location based upon the angle of reflection.

In the bottom pathway, the resulting voltage signal from the TIA 408 is also received at a summing junction 420, and this analog voltage signal sum is fed into an analog to digital converter 422 and converted into a digital signal sum. The digital signal may undergo a gamma correction operation, at 424, e.g. to transform a luminance of linear red, green, and blue components into a nonlinear image signal. This stage then provides the signal into a greyscale image frame buffer 426.

In the above examples, the scanning mirror may be a sine-wave mirror system that scans in a first direction (e.g. an x-direction) faster than in a second orthogonal direction (e.g. a y-direction). Due to the harmonic oscillation of the mirror, the speed of the mirror slows to a stop at the vertical and horizontal edges of the mirror motion at one point in time, resulting in unnecessarily higher power density at the edges. As such, in some examples, sinusoidal correction may be applied to the system by turning off the infrared light source when the scanning mirror is scanning at the edges, and turning the infrared light source on when it is in an active area. Such a correction function may further help to conserve power.

Additionally, with such a harmonically oscillating mirror system, the mirror motion has a greater speed in the center of the motion than at the edges of the motion. As such, if a constant sample rate is utilized for gaze tracking, more gaze signals are sampled at the edges of the image than in the center, resulting in variable resolution across the image. As such, in some examples the system may be configured to utilize a variable sample rate to compensate for the variable mirror speed and thus to achieve a more even resolution across the image.

Further, in some examples, the eye tracking laser light source may be illuminated only for sufficient time to obtain each sample, and turned off between samples. This further may help to reduce power consumption by the laser and current-to-voltage converters.

Figure 5A:
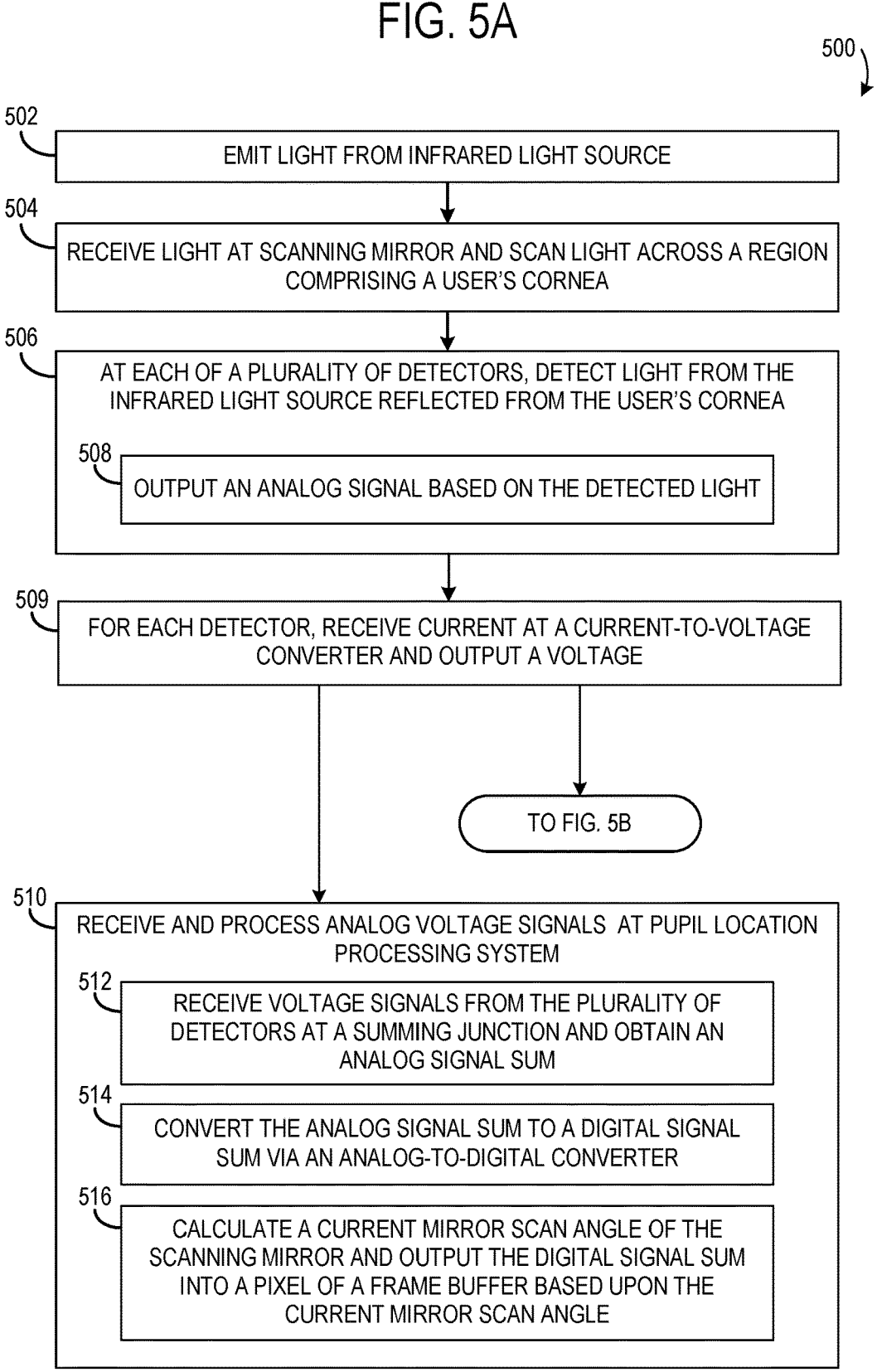
FIGS. 5A-B show a flow diagram illustrating an example method for eye tracking.
Figure 5B:
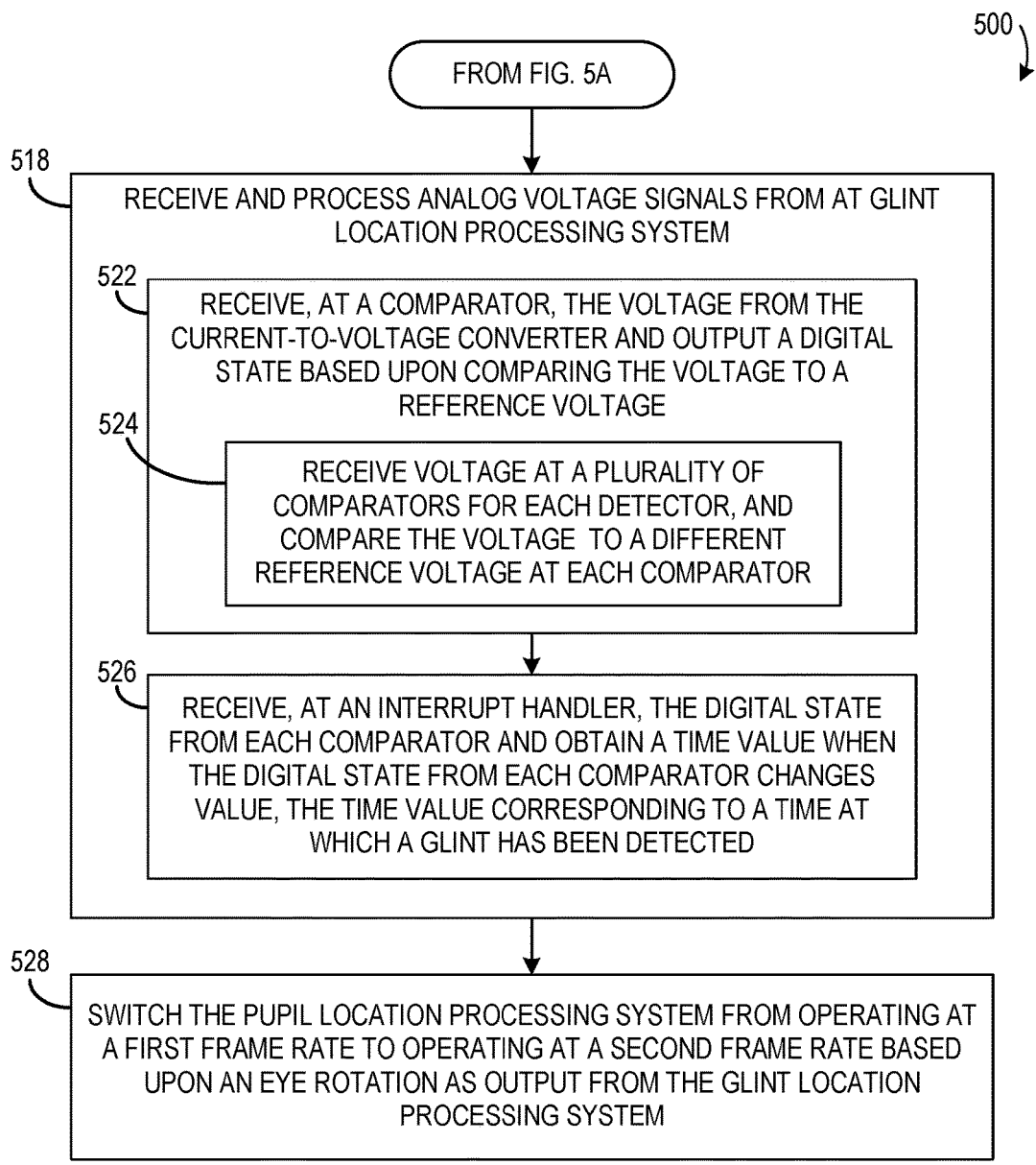

FIGS. 5A and 5B show an example method 500 for performing eye tracking on a near-eye display system. Method 500 includes, at 502, emitting light from an infrared light source, such as a laser or other suitable light source, and at 504, receiving the light at a scanning mirror system and scanning the light across a region comprising a user's cornea. As the light is scanned across the eye, the light reflects from the cornea both diffusely and specularly. Method 500 further includes, at each of a plurality of photodetectors, detecting light from the infrared light source as reflected from the user's cornea, as shown at 506. Each photodetector of the plurality of photodetectors outputs an analog signal based on the detected light, at 508.

At 509, method 500 comprises, for each photodetector, receiving the analog current signal at a current to voltage converter, and outputting a corresponding voltage. The analog voltage signals are received and processed at a pupil location processing system, at 510, and also at a glint location processing system, described with regard to FIG. 5B.

Processing at the pupil location processing system may include, at 512, receiving the analog signals at a summing junction and obtaining an analog signal sum, and at 514, converting the analog signal sum to a digital signal sum via an analog-to-digital converter. The pupil location processing system then calculates a current mirror scan angle of the scanning mirror, and outputs the digital signal sum into a pixel of a frame buffer based upon the current mirror scan angle, at 516.

Continuing with FIG. 5B, method 500 also includes receiving and processing the analog signals from the plurality of photodetectors at a glint location processing system, at 518. Processing at the glint location processing system may include, receiving each analog voltage output by the current-to-voltage converters at a comparator, and outputting a digital state based upon comparing each voltage to a reference voltage, at 522. In some examples, a plurality of comparators may be utilized for each photodetector, such that the voltage obtained for each photodetector is compared to a different reference voltage at each of the plurality of comparators, at 524, to thus determine a magnitude of the analog voltage with more accuracy. Processing at the glint location processing system further may include, at 526, receiving at an interrupt handler the digital state from each comparator, and triggering an interrupt to obtain a time value when the digital state from each comparator changes value, the time value corresponding to a time at which a glint has been detected. This value may then be used to obtain a scanning mirror angle to determine an angle at which a glint is detected. In examples where a plurality of comparators are utilized for each photodetector, time values may be recorded specifically for each comparator, such that a change in signal magnitude from each photodetector may be tracked more accurately and granularly.

As described above, the pupil location processing system may utilize more power during operation than the glint location processing system operating at a same frame rate, as pupil location processing involves image processing and analysis. As such, method 500 further may include, at 528, switching the pupil location processing system from operating at a first frame rate operating at a second frame rate based upon output from the glint location processing system. For example, upon detecting that an eye rotation has exceeded a threshold motion based upon output from the glint location processing system, the pupil location processing system may switch from operating at a lower frame rate (which may include a disabled state) to a higher frame rate. Further, when the pupil location is updated, the pupil location processing system may switch back to operating at a lower frame rate, until the eye rotation again exceeds the threshold motion.

In some embodiments, the methods and processes described herein may be tied to a computing system of one or more computing devices. In particular, such methods and processes may be implemented as a computer-application program or service, an application-programming interface (API), a library, and/or other computer-program product.

Figure 6:
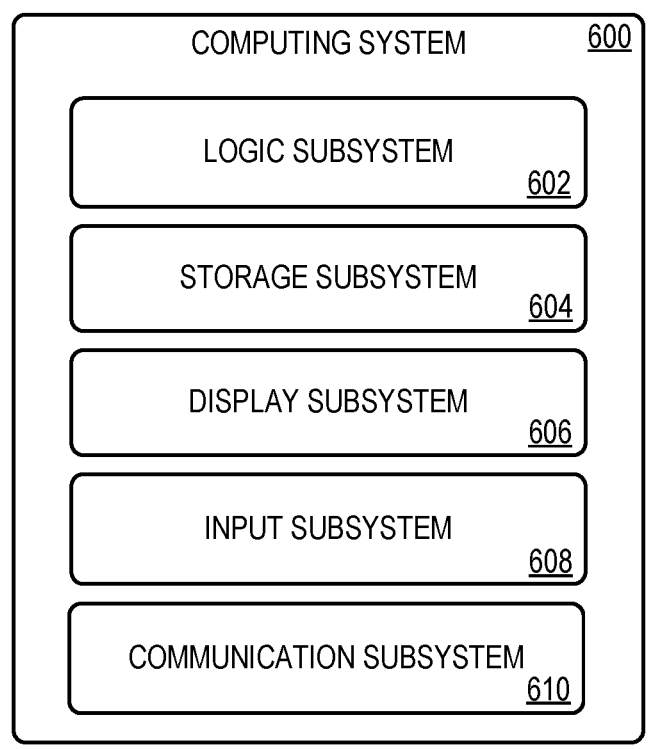
FIG. 6 shows a block diagram of an example computing system.

FIG. 6 schematically shows a non-limiting embodiment of a computing system 600 that can enact one or more of the methods and processes described above. Computing system 600 is shown in simplified form. Computing system 600 may take the form of one or more personal computers, server computers, tablet computers, home-entertainment computers, network computing devices, gaming devices, mobile computing devices, mobile communication devices (e.g., smart phone), and/or other computing devices.

Computing system 600 includes a logic subsystem 602 and a storage subsystem 604. Computing system 600 may optionally include a display subsystem 606, input subsystem 608, communication subsystem 610, and/or other components not shown in FIG. 6. Near-eye display device 102 is an example of computing system 600. Further, the processing systems as disclosed herein, including the glint location processing system, pupil location processing system may be implemented via computing system 600.

Logic subsystem 602 includes one or more physical devices configured to execute instructions. For example, the logic subsystem 602 may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic subsystem 602 may include one or more processors configured to execute software instructions. Additionally or alternatively, the logic subsystem 602 may include one or more hardware or firmware logic machines configured to execute hardware or firmware instructions. Processors of the logic subsystem 602 may be single-core or multi-core, and the instructions executed thereon may be configured for sequential, parallel, and/or distributed processing. Individual components of the logic subsystem 602 optionally may be distributed among two or more separate devices, which may be remotely located and/or configured for coordinated processing. Aspects of the logic subsystem 602 may be virtualized and executed by remotely accessible, networked computing devices configured in a cloud-computing configuration.

Storage subsystem 604 includes one or more physical devices configured to hold instructions executable by the logic subsystem 602 to implement the methods and processes described herein. When such methods and processes are implemented, the state of storage subsystem 604 may be transformed—e.g., to hold different data.

Storage subsystem 604 may include removable and/or built-in devices. Storage subsystem 604 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage subsystem 604 may include volatile, nonvolatile, dynamic, static, read/write, read-only, random-access, sequential-access, location-addressable, file-addressable, and/or content-addressable devices.

It will be appreciated that storage subsystem 604 includes one or more physical devices. However, aspects of the instructions described herein alternatively may be propagated by a communication medium (e.g., an electromagnetic signal, an optical signal, etc.) that is not held by a physical device for a finite duration.

Aspects of logic subsystem 602 and storage subsystem 604 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

When included, display subsystem 606 may be used to present a visual representation of data held by storage subsystem 604. This visual representation may take the form of a graphical user interface (GUI). As the herein described methods and processes change the data held by the storage subsystem 604, and thus transform the state of the storage subsystem 604, the state of display subsystem 606 may likewise be transformed to visually represent changes in the underlying data. Display subsystem 606 may include one or more display devices utilizing virtually any type of technology. Such display devices may be combined with logic subsystem 602 and/or storage subsystem 604 in a shared enclosure, or such display devices may be peripheral display devices.

When included, input subsystem 608 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 610 may be configured to communicatively couple computing system 600 with one or more other computing devices. Communication subsystem 610 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 600 to send and/or receive messages to and/or from other devices via a network such as the Internet.

Another example provides an eye tracking system, comprising an infrared light source, scanning optics configured to scan light from the infrared light source across a region comprising a user's cornea, and a plurality of photodetectors, each photodetector being configured to detect infrared light reflected from the user's cornea at a corresponding angle. The scanning optics may additionally or alternatively include a scanning mirror system. The eye tracking system may additionally or alternatively include a pupil location processing system comprising a summing junction configured to sum analog signals received from the plurality of photodetectors to obtain an analog signal sum, an analog to digital converter configured to convert the analog signal sum to a digital signal sum, and a scanning mirror trajectory calculator configured to calculate a current mirror pointing angle of a scanning mirror of the scanning optics and output the digital signal sum into a pixel of a frame buffer based upon the current mirror scan angle. The eye tracking system may additionally or alternatively include, for each photodetector, a current to voltage converter configured to output a voltage based upon a current received from the photodetector, and the eye tracking system may additionally or alternatively include a glint location processing system, the glint location processing system comprising, for each photodetector, a comparator configured to receive the voltage from the current to voltage converter and output a digital state based upon comparing the voltage to a reference voltage, and an interrupt handler configured to receive the digital state from each comparator and to obtain a time value when the digital state from each comparator changes value, the time value corresponding to a time at which a glint has been detected by a photodetector. The pupil location processing system may additionally or alternatively be configured to switch from operating at a lower frame rate to operating at a higher frame rate upon detecting that an eye rotation has exceeded a threshold motion based upon output from the glint location processing system. The glint location processing system The eye tracking system may additionally or alternatively include a plurality of comparators for each photodetector, each comparator being configured to compare voltage received from the current to voltage converter to a different reference voltage, and for each photodetector, a serializer configured to serialize outputs of the plurality of comparators for the photodetector. Additionally or alternatively, the glint location processing system may have a different gain than a gain of the pupil location processing system. The pupil location processing system may additionally or alternatively be configured to output a grayscale image of a user's pupil. The eye tracking system may additionally or alternatively include a sampling handler configured to turn the infrared light source on and off on a pixel-by-pixel basis. Two or more of the plurality of photodetectors may additionally or alternatively be configured to detect light of a different wavelengths.

Another example provides an eye tracking system comprising an infrared light source, a scanning mirror configured to scan light from the infrared light source across a region comprising a user's cornea, a plurality of photodetectors, each photodetector being configured to detect light from the infrared light source reflected from the user's cornea at a corresponding angle and output an analog signal based on the detected light, and a pupil location processing system comprising a summing junction configured to sum analog signals received from the plurality of photodetectors to obtain an analog signal sum, an analog to digital converter configured to convert the analog signal sum to a digital signal sum, and a scanning mirror trajectory calculator configured to calculate a current mirror scan angle of the scanning mirror and output the digital signal sum into a pixel of a frame buffer based upon the current mirror pointing angle. The pupil location processing system may additionally or alternatively be configured to output a grayscale image of a user's pupil. The eye tracking system may additionally or alternatively include, for each photodetector, a current to voltage converter configured to output a voltage based upon a current received from the photodetector, and the eye tracking system may additionally or alternatively include a glint location processing system, the glint location processing system comprising, for each photodetector, a comparator configured to receive the voltage from the current to voltage converter and output a digital state based upon comparing the voltage to a reference voltage, and an interrupt handler configured to receive the digital state of each comparator and output a time value when the digital state output by a comparator triggers the interrupt handler, the time value corresponding to a time at which a glint has been detected. The pupil location processing system may additionally or alternatively be configured to change from operating at a lower frame rate to operating at a higher frame rate upon detecting a pupil motion has exceeded a threshold motion based upon output from the glint location processing system. The glint location processing system may additionally or alternatively include a plurality of comparators for each photodetector, each comparator being configured to compare voltage received from the current to voltage converter to a different reference voltage. The eye tracking system may additionally or alternatively include, for each photodetector, a serializer configured to serialize outputs of the plurality of comparators for the photodetector. The eye tracking system may additionally or alternatively sampling logic configured to turn the infrared light source on and off on a pixel-by-pixel basis.

Another example provides an eye tracking system comprising an infrared light source, a scanning mirror configured to scan light from the infrared light source across a region comprising a user's cornea, a plurality of photodetectors, each photodetector configured to detect light from the infrared light source reflected from the user's cornea at a corresponding angle and output an analog signal based on the detected light, for each photodetector, a current to voltage converter configured to output a voltage based upon a current received from the photodetector, and a glint location processing system comprising, a comparator configured to receive the voltage from the current to voltage converter and output a digital state based upon comparing the voltage to a reference voltage, and an interrupt handler configured to receive the digital state of each comparator and output a time value when the digital state output by a comparator triggers the interrupt handler, the time value corresponding to a time at which a glint has been detected by a photodetector. The eye tracking system may additionally or alternatively include a pupil location processing system comprising a summing junction configured to sum analog signals received from the plurality of photodetectors to obtain an analog signal sum, a converter configured to convert the analog signal sum to a digital signal sum, and a scanning mirror trajectory calculator configured to calculate a current mirror pointing angle of the scanning mirror and output the digital signal sum into a pixel of a frame buffer based upon the current mirror pointing angle. The glint location processing system may additionally or alternatively be configured to detect a glint from a region of a tear duct.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. An eye tracking system, comprising:
    an infrared light source;
    scanning optics configured to scan light from the infrared light source across a region comprising a user's cornea; and
    a plurality of photodetectors, each photodetector being configured to detect infrared light reflected from the user's cornea at a corresponding angle; and
    a pupil location processing system comprising:
        a summing junction configured to sum analog signals received from the plurality of photodetectors to obtain an analog signal sum,
        an analog to digital converter configured to convert the analog signal sum to a digital signal sum, and
        a scanning mirror trajectory calculator configured to calculate a current mirror pointing angle of a scanning mirror of the scanning optics and output the digital signal sum into a pixel of a frame buffer based upon the current mirror scan angle.

2. The eye tracking system of claim 1, wherein the scanning optics comprise a scanning mirror system.

3. The eye tracking system of claim 1, further comprising, for each photodetector, a current to voltage converter configured to output a voltage based upon a current received from the photodetector, and the eye tracking system further comprising a glint location processing system, the glint location processing system comprising,
    for each photodetector, a comparator configured to receive the voltage from the current to voltage converter and output a digital state based upon comparing the voltage to a reference voltage; and
    an interrupt handler configured to receive the digital state from each comparator and to obtain a time value when the digital state from each comparator changes value, the time value corresponding to a time at which a glint has been detected by a photodetector.

4. The eye tracking system of claim 3, wherein the pupil location processing system is configured to switch from operating at a lower frame rate to operating at a higher frame rate upon detecting that an eye rotation has exceeded a threshold motion based upon output from the glint location processing system.

5. The eye tracking system of claim 3, wherein the glint location processing system comprises a plurality of comparators for each photodetector, each comparator being configured to compare voltage received from the current to voltage converter to a different reference voltage.

6. The eye tracking system of claim 1, wherein the glint location processing system has a different gain than the pupil location processing system.

7. The eye tracking system of claim 1, wherein the pupil location processing system is configured to output a grayscale image of a user's pupil.

8. The eye tracking system of claim 1, further comprising a sampling handler configured to turn the infrared light source on and off on a pixel-by-pixel basis for pixels of the frame buffer.

9. The eye tracking system of claim 1, wherein two or more of the plurality of photodetectors are configured to detect light of a different wavelengths.

10. An eye tracking system, comprising:
    an infrared light source;
    a scanning mirror configured to scan light from the infrared light source across a region comprising a user's cornea;
    a plurality of photodetectors, each photodetector being configured to detect light from the infrared light source reflected from the user's cornea at a corresponding angle and output an analog signal based on the detected light; and
    a pupil location processing system comprising a summing junction configured to sum analog signals received from the plurality of photodetectors to obtain an analog signal sum, an analog to digital converter configured to convert the analog signal sum to a digital signal sum, and a scanning mirror trajectory calculator configured to calculate a current mirror scan angle of the scanning mirror and output the digital signal sum into a pixel of a frame buffer based upon the current mirror pointing angle.

11. The eye tracking system of claim 10, wherein the pupil location processing system is configured to output a grayscale image of a user's pupil.

12. The eye tracking system of claim 10, further comprising, for each photodetector, a current to voltage converter configured to output a voltage based upon a current received from the photodetector, and the eye tracking system further comprising a glint location processing system, the glint location processing system comprising,
for each photodetector, a comparator configured to receive the voltage from the current to voltage converter and output a digital state based upon comparing the voltage to a reference voltage; and
an interrupt handler configured to receive the digital state of each comparator and output a time value when the digital state output by a comparator triggers the interrupt handler, the time value corresponding to a time at which a glint has been detected.

13. The eye tracking system of claim 12, wherein the pupil location processing system is configured to change from operating at a lower frame rate to operating at a higher frame rate upon detecting a pupil motion has exceeded a threshold motion based upon output from the glint location processing system.

14. The eye tracking system of claim 12, wherein the glint location processing system comprises a plurality of comparators for each photodetector, each comparator being configured to compare voltage received from the current to voltage converter to a different reference voltage.

15. The eye tracking system of claim 14, further comprising, for each photodetector, a serializer configured to serialize outputs of the plurality of comparators for the photodetector.

16. The eye tracking system of claim 12, further comprising sampling logic configured to turn the infrared light source on and off on a pixel-by-pixel basis for pixels of the frame buffer.

17. An eye tracking system comprising
an infrared light source;
a scanning mirror configured to scan light from the infrared light source across a region comprising a user's cornea;
a plurality of photodetectors, each photodetector configured to detect light from the infrared light source reflected from the user's cornea at a corresponding angle and output an analog signal based on the detected light;
for each photodetector, a current to voltage converter configured to output a voltage based upon a current received from the photodetector, and
a glint location processing system comprising,
a comparator configured to receive the voltage from the current to voltage converter and output a digital state based upon comparing the voltage to a reference voltage, and
an interrupt handler configured to receive the digital state of each comparator and output a time value when the digital state output by a comparator triggers the interrupt handler, the time value corresponding to a time at which a glint has been detected by a photodetector.

18. The eye tracking system of claim 17, further comprising
a pupil location processing system comprising
a summing junction configured to sum analog signals received from the plurality of photodetectors to obtain an analog signal sum,
a converter configured to convert the analog signal sum to a digital signal sum, and
a scanning mirror trajectory calculator configured to calculate a current mirror pointing angle of the scanning mirror and output the digital signal sum into a pixel of a frame buffer based upon the current mirror pointing angle.

19. The eye tracking system of claim 17, wherein the glint location processing system is configured to detect a glint from a region of a tear duct.

* * * * *